(12) United States Patent
Mitragotri et al.

(10) Patent No.: US 8,642,664 B2
(45) Date of Patent: Feb. 4, 2014

(54) COMPOSITION FOR SOLUBILIZING TISSUE AND CELLS COMPRISING N-TETRADECYL-N,N-DIMETHYL-3-AMMONIO-1-PROPANE-SULFONATE AND POLYOXYETHYLENE (10) CETYL ETHER

(76) Inventors: Samir Mitragotri, Santa Barbara, CA (US); Russell M. Lebovitz, San Diego, CA (US); Byeong Hee Hwang, Goleta, CA (US)

( * ) Notice: Subject to any disclaimer, the term of this patent is extended or adjusted under 35 U.S.C. 154(b) by 47 days.

(21) Appl. No.: 13/473,261

(22) Filed: May 16, 2012

(65) Prior Publication Data

US 2012/0253238 A1 Oct. 4, 2012

Related U.S. Application Data

(63) Continuation-in-part of application No. 13/095,639, filed on Apr. 27, 2011, now Pat. No. 8,389,582, which is a continuation-in-part of application No. 12/664,994, filed as application No. PCT/US2008/072384 on Aug. 6, 2008, said application No. 13/095,639 is a continuation-in-part of application No. 13/126,105, filed as application No. PCT/US2010/024010 on Feb. 12, 2010.

(60) Provisional application No. 60/963,773, filed on Aug. 6, 2007, provisional application No. 61/152,585, filed on Feb. 13, 2009.

(51) Int. Cl.
*A01N 31/14* (2006.01)
*A01N 33/12* (2006.01)
*A61N 1/30* (2006.01)
*A61B 10/00* (2006.01)

(52) U.S. Cl.
USPC .............. 514/723; 514/642; 600/562; 604/20

(58) Field of Classification Search
None
See application file for complete search history.

(56) References Cited

U.S. PATENT DOCUMENTS

| | | | |
|---|---|---|---|
| 4,268,613 A | 5/1981 | Okishi | |
| 5,398,690 A | 3/1995 | Batten et al. | |
| 5,492,126 A | 2/1996 | Hennige et al. | |
| 5,696,069 A | 12/1997 | Ito et al. | |
| 5,739,432 A | 4/1998 | Sinha | |
| 5,804,452 A | 9/1998 | Pronovost et al. | |
| 5,913,833 A | 6/1999 | Elstrom et al. | |
| 6,007,497 A | 12/1999 | Huitema | |
| 6,093,551 A | 7/2000 | Raithel et al. | |
| 6,165,500 A | 12/2000 | Cevc | |
| 6,328,728 B1 | 12/2001 | Holladay et al. | |
| 6,544,211 B1 | 4/2003 | Andrew et al. | |
| 6,560,478 B1 | 5/2003 | Alfano et al. | |
| 6,589,173 B1 | 7/2003 | Mitragotri | |
| 2002/0082518 A1 | 6/2002 | Weiss et al. | |
| 2003/0060818 A1 | 3/2003 | Kannenberg et al. | |
| 2003/0143116 A1 | 7/2003 | Zheng et al. | |
| 2003/0211520 A1 | 11/2003 | Afar et al. | |
| 2004/0151745 A1 | 8/2004 | Zimmer et al. | |
| 2005/0164903 A1 | 7/2005 | Ko et al. | |
| 2005/0214825 A1 | 9/2005 | Stuelpnagle | |
| 2006/0046261 A1 | 3/2006 | Porter et al. | |
| 2006/0100569 A1 | 5/2006 | McRury et al. | |
| 2006/0165823 A1 | 7/2006 | Herrera | |
| 2006/0166222 A1 | 7/2006 | Lu et al. | |
| 2007/0055181 A1 | 3/2007 | Deem et al. | |
| 2007/0055261 A1 | 3/2007 | Reiley et al. | |
| 2007/0059687 A1 | 3/2007 | Ohno et al. | |
| 2007/0173448 A1 | 7/2007 | Shah et al. | |
| 2010/0261176 A1 | 10/2010 | Mitragotri et al. | |

FOREIGN PATENT DOCUMENTS

EP 0743519 A2 11/1996

OTHER PUBLICATIONS

Tutulan-Cunita et al., "Mutational analysis of the yeast multidrug resistance ABC transporter Pdr5p with altered drug specificity", Genes to cells (2005) vol. 10, pp. 409-420.
Pubchem polidocanol (pubchem.ncbi.nlm.nih.gov/summary/summary.cgi?cid=24750&loc=ec_rcs, downloaded Oct. 29, 2012.
Huang et al., "Separation and measurement of desmosine and isodesmosine in vascular tissue hydrolysates by micellar electrokinetic capillary chromatography with a mixed micelle system", J. Chromaography A 1175 : 294-296 (2007).
Written Opinion and International Search Report of the International Searching Authority from related PCT Application No. PCT/US08/72384.
Ayliffe, et al. "Hand disinfection: a comparison of various agents in laboratory and ward studies" J. Hospital Infection, 1988, 11, 226-243.

*Primary Examiner* — Sandra Saucier
(74) *Attorney, Agent, or Firm* — Benjamen E. Kern

(57) ABSTRACT

Solubilizing compositions are provided. The compositions comprise at least one zwitterionic surfactant and at least one nonionic surfactant. In one embodiment, the compositions may be useful for solubilizing and remodeling and/or removing tissue on or beneath a patient's skin, optionally in conjunction with the application of energy to a region of interest on the skin. In one embodiment, at least one analyte may be collected and analyzed from the solubilized tissue.

20 Claims, 10 Drawing Sheets

COMPOSITION FOR SOLUBILIZING TISSUE AND CELLS COMPRISING N-TETRADECYL-N,N-DIMETHYL-3-AMMONIO-1-PROPANE-SULFONATE AND POLYOXYETHYLENE (10) CETYL ETHER

CROSS-REFERENCE TO RELATED APPLICATIONS

This application is a continuation-in-part application of U.S. patent application Ser. No. 13/095,639, filed on Apr. 27, 2011. U.S. patent application Ser. No. 13/095,639 is a continuation-in-part application of U.S. patent application Ser. No. 12/664,994, filed on Jun. 29, 2010 as a U.S. National Stage filing of PCT/US2008/072384, filed on Aug. 6, 2008, which, in turn, claims priority to U.S. Provisional Patent Application Ser. No. 60/963,773, filed on Aug. 6, 2007, and now expired. U.S. patent application Ser. No. 13/095,639 is also a continuation-in-part application of 13/126,105, filed on Apr. 26, 2011 as a U.S. National Stage filing of PCT/US2010/024010, filed on Feb. 12, 2010, which, in turn, claims priority to U.S. Provisional Patent Application Ser. No. 61/152,585, filed on Feb. 13, 2009, and now expired. All of these related applications are incorporated by reference herein in their entireties.

STATEMENT REGARDING FEDERALLY SPONSORED RESEARCH OR DEVELOPMENT

This invention was made with government support under federal grant number W81XWH-06-01-00400 awarded by the United States Army. The United States Government has certain rights in this invention.

BACKGROUND

Skin is the "window" to the body. Skin is unique among the body's organs for several reasons: (1) skin is the largest organ of the human body; (2) skin is directly exposed to the environment; (3) skin is an excellent excretory organ; (4) skin is the most visible and accessible organ of the body; and (5) skin is a highly active immune organ of the body.

Skin has another important quality: The molecular profile of skin has information that is valuable for physiological monitoring of, among other things, small organic molecules, proteins, DNA, RNA, and lipids. Much can be learned from skin's molecular profiling. For example, pathogens (e.g., bacteria) that grow on skin may allow for forensic identification. Skin's molecular profile may reveal environmental factors to which the body has been passively exposed. These environmental factors may range from the mundane, e.g., allergens, toxins, and cosmetic products, to the industrial and/or agricultural, e.g., industrial solvents, fertilizers, and pesticides, to the dangerous, e.g., explosives and other warfare agents.

Skin's molecular profile may also reveal factors to which the body has been actively exposed. More particularly, skin's molecular profile may reveal what the body has consumed. For example, abused substances (e.g., illegal drugs or narcotics) and therapeutic drugs (e.g., tramadol, fluconazole, barbitals, and anabolic steroids) may be found in skin weeks after consumption.

Skin's molecular profile may also aid diagnosis of conditions and diseases. For example, skin cholesterol is a proxy of the extent of arterial blocks. Glycation of skin collagen is an indicator of a history of diabetes. Skin deposition of β-amyloids may indicate the existence and extent of Alzheimer's disease. And skin globular proteins (e.g., IgE) may indicate allergies to specific allergens.

Several methods exist for sampling biomolecules from skin. For example, one current method is skin biopsy. However, skin biopsy is invasive and analysis is difficult. Practically speaking, skin biopsy is designed for well-equipped experts and, thus, its use in a point-of-care setting is limited. Another current method for sampling biomolecules from skin, tape stripping, suffers from these same limitations and is generally unacceptable because of variability in results. Yet another current method for sampling biomolecules from skin is taking a skin swab. While desirable because of its simplicity, a skin swab is superficial in its depth of inspection, and qualitative in its results. Finally, tissue has been subjected to ultrasound in the presence of surfactants such as sorbitans ("SPANs"), polyoxyethelene sorbitans combined with fatty acids ("tweens"), cetyl trimethylammonium bromide ("CTAB"), and their mixtures. See U.S. Pat. No. 6,589,173 issued to Mitragotri et al. However, SPANs, tweens, and CTAB, individually and collectively, have been found to be unsuitable to recover skin constituents. Sorbitans and tweens, which are nonionic surfactants, are mild and non-denaturing in character, but are ineffective to solubilize skin tissue. CTAB, a cationic surfactant, is effective to solubilize skin tissue, but unsuitably denatures proteins, profoundly changing properties of biomolecules in solution, rendering them unusable for functional purposes.

Along with providing a cornucopia of information, skin can also be a host to myriad undesirable cosmetic conditions, such as age spots, skin tags, seborrheic keratosis, scar tissues, xanthomas, non-cancerous hyperproliferative conditions, surface bumps, and scaly patches; and therapeutic conditions such as skin tumors, actinic keratosis, leukoplakia, and surface cancers relating to Barrett's esophagus and right-colon pre-cancer plaque. For these conditions, solubilization and remodeling or removal may be the primary concern, with or without subsequent diagnostic processing.

A need exists for compositions for skin sampling, as well as for mucosal membrane and other tissue sampling, which, when used in conjunction with applied energy, at least partially solubilize such skin, mucosal membrane, and other tissue. A further need exists to preserve the functionality and structural integrity of analytes, including biomolecules, obtained from the solubilized skin, mucosal membrane, and other tissue.

SUMMARY

In one embodiment, a composition is provided, the composition comprising:
a zwitterionic surfactant, comprising:

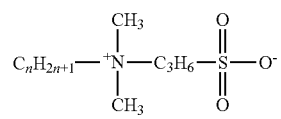

wherein n=10, 12, 14, 16, or 18; and
a non-ionic surfactant, comprising:

wherein a=12 or 16, and wherein b=2, 4, 10, 20, or 23.

In one embodiment, n=12 (corresponding to N-dodecyl-N, N-dimethyl-3-ammonio-1-propanesulfonate or "DDPS"), a=16, and b=10 (corresponding to polyoxyethylene (10) cetyl ether or "Brij C10").

In one embodiment, n=14 (corresponding to N-tetradecyl-N,N-dimethyl-3-ammonio-1-propanesulfonate or "TPS"), a=12, and b=4 (corresponding to polyoxyethylene (4) lauryl ether or "Brij 30"). In another embodiment, n=14 (TPS), a=16, and b=2 (corresponding to polyoxyethylene (2) cetyl ether or "Brij 52"). In another embodiment, n=14 (TPS), a=16, and b=10 (Brij C10).

In one embodiment, n=16 (corresponding to N-hexadecyl-N,N-dimethyl-3-ammonio-1-propanesulfonate or "HPS"), a=12, and b=4 (Brij 30). In another embodiment, n=16 (HPS), a=16, and b=2 (Brij 52). In another embodiment, n=16 (HPS), a=16, and b=10 (Brij C10).

In one embodiment, n=18 (corresponding to N-octadecyl-N,N-dimethyl-3-ammonio-1-propanesulfonate or "OPS"), a=12, and b=4 (Brij 30). In another embodiment, n=18 (OPS), a=16, and b=2 (Brij 52). In another embodiment, n=18 (OPS), a=16, and b=10 (Brij C10). In another embodiment, n=18 (OPS), a=16, and b=20 (corresponding to polyoxyethylene (20) cetyl ether or "Brij 58").

In one embodiment, a method is provided for solubilizing and remodeling and/or removing tissue on or beneath a patient's skin, comprising optionally applying energy to a region of interest on the skin; and contacting the region with a tissue solubilizing composition.

In another embodiment, a method for recovering analytes from mucosal membrane, skin, or other tissue is provided, the method comprising: optionally applying energy to a region of interest on the mucosal membrane, skin, or other tissue containing at least one analyte; contacting the region with a tissue solubilizing composition, thereby solubilizing at least some of the mucosal membrane, skin, or other tissue containing at least one analyte; and collecting the at least one analyte from the solubilized mucosal membrane, skin, and other tissue.

BRIEF DESCRIPTION OF THE DRAWINGS

In the accompanying figures, experimental data are given that, together with the detailed description provided below, describe example embodiments of the claimed invention.

DETAILED DESCRIPTION

Figure 1:
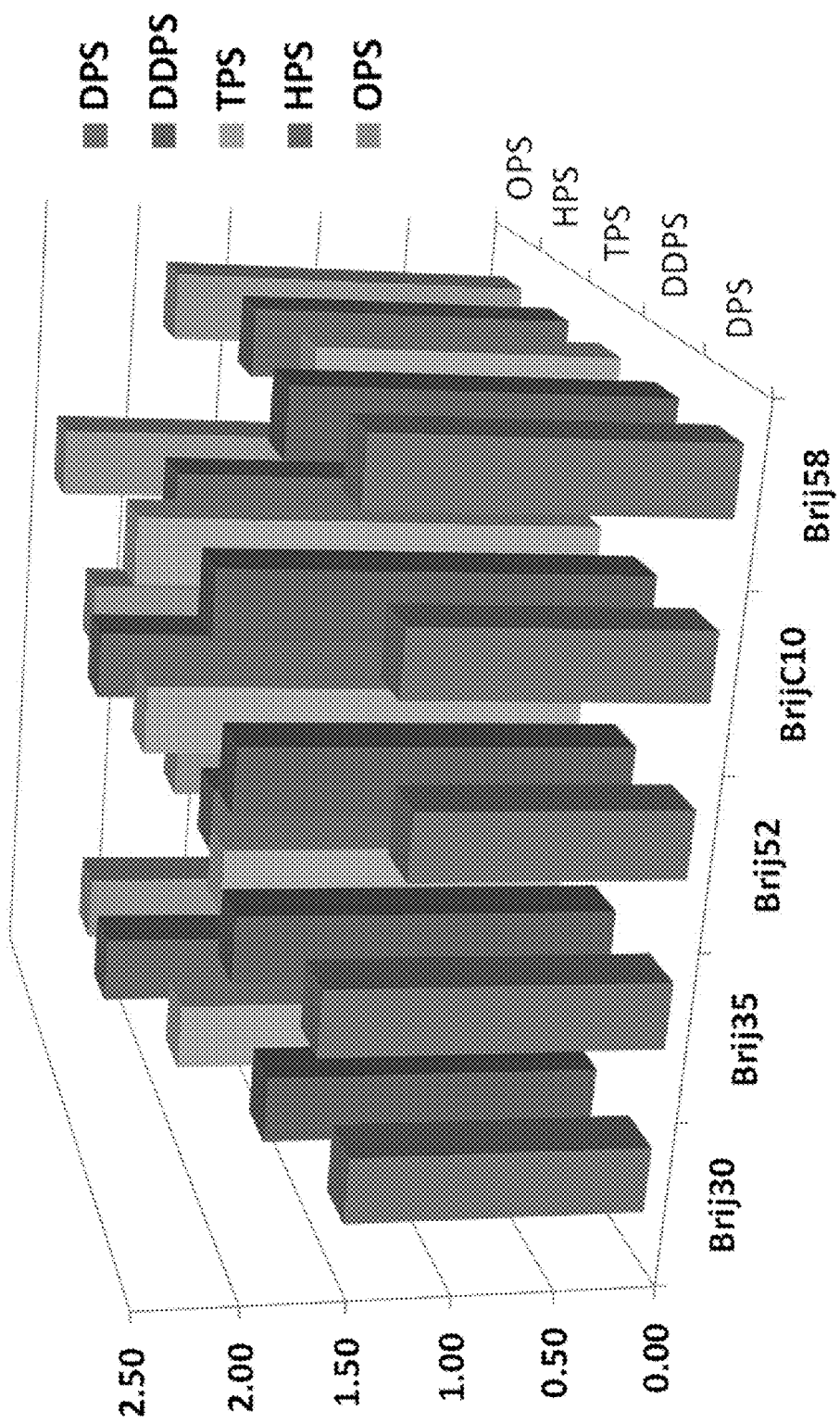
FIG. 1 illustrates in graphical form the total protein (mg/ml) recovered from porcine skin when the porcine skin is contacted with various combinations of zwitterionic and non-ionic surfactants in the presence of ultrasound.

In one embodiment, a composition is provided, the composition comprising:
a zwitterionic surfactant, comprising:

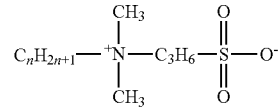

wherein n=10, 12, 14, 16, or 18; and
a non-ionic surfactant, comprising:

wherein a=12 or 16, and wherein b=2, 4, 10, 20, or 23.

In one embodiment, the zwitterionic surfactant comprises DPS and the nonionic surfactant comprises at least one of Brij 30, Brij 35, Brij 52, Brij C10, and Brij 58. In one embodiment, the combination of DPS:Brij 30 is excluded.

In another embodiment, the zwitterionic surfactant comprises DDPS and the nonionic surfactant comprises at least one of Brij 30, Brij 35, Brij 52, Brij C10, and Brij 58.

In another embodiment, the zwitterionic surfactant comprises TPS and the nonionic surfactant comprises at least one of Brij 30, Brij 35, Brij 52, Brij C10, and Brij 58.

In another embodiment, the zwitterionic surfactant comprises HPS and the nonionic surfactant comprises at least one of Brij 30, Brij 35, Brij 52, Brij C10, and Brij 58. In one embodiment, the combination of HPS:Brij 35 is excluded.

In another embodiment, the zwitterionic surfactant comprises OPS and the nonionic surfactant comprises at least one of Brij 30, Brij 35, Brij 52, Brij C10, and Brij 58.

The zwitterionic surfactant and the nonionic surfactant may be dissolved in a buffer solution. The buffer solution may comprise, for example, one or more of phosphate-buffered saline (PBS) (pH=7.2-7.6), tris-buffered saline (pH=7.4-8.0), tris-hydrochloride (7.0-9.0), and ethylenediaminetetraacetic acid (EDTA) (pH=7.4-9.0). Thus, the surfactant combination may have a pH of greater than about 7.0 in buffer solution, between about 7.0 and 9.0 in buffer solution, between about 7.4 and 9.0 in buffer solution, between about 7.4 and 8.0 in buffer solution, and between about 7.2 and 7.6 in buffer solution.

The zwitterionic surfactant and the nonionic surfactant may be present in a total concentration of between about 0.01% and about 10% (w/v) in the buffer solution. For example, the zwitterionic surfactant and the nonionic surfactant may be present in a total concentration of about 0.01% to about 5% (w/v) in the buffer solution, including total concentrations of about 0.1% (w/v) to about 2% (w/v) in the buffer solution, about 1% (w/v) in the buffer solution, and about 0.1% (w/v) to about 0.5% (w/v) in the buffer solution. In one embodiment, the zwitterionic surfactant and the nonionic surfactant are present in a total concentration of about 0.5% (w/v) in the buffer solution. In another embodiment, the zwitterionic surfactant and the nonionic surfactant may be present in a ratio of about 3:1 to about 1:3 or about 3:2 to about 2:3. In one embodiment, the zwitterionic surfactant and the nonionic surfactant may be present in a ratio of about 1:1.

The zwitterionic surfactant:nonionic surfactant composition may have several applications.

For example, in one embodiment, a method is provided for solubilizing and remodeling and/or removing tissue on or beneath a patient's skin, comprising applying energy to a region of interest on the skin; and contacting the region with a tissue solubilizing composition comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58.

In another embodiment, a method for recovering analytes from mucosal membrane, skin, or other tissue is provided, the method comprising: applying energy to a region of interest on the mucosal membrane, skin, or other tissue containing at least one analyte; contacting the region with a tissue solubilizing composition, the tissue solubilizing composition comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, thereby solubilizing at least some of the mucosal membrane, skin, or other tissue containing at least one analyte; and collecting the at least one analyte from the solubilized mucosal membrane, skin, and other tissue.

In some embodiments, "other tissue" may include breast, prostate, eye, vagina, bladder, nail, hair, colon, testicles, intestine, lung, brain, pancreas, liver, heart, bone, or aorta wall.

In some embodiments, an "analyte" may include any biomolecule, drug, small molecule, warfare agent, environmental contaminant, microbe, and the like that is present in or on the tissue and can be extracted from the tissue of interest.

In some embodiments, "biomolecules" may include proteins (e.g., disease biomarkers such as cancer biomarkers, antibodies: IgE, IgG, IgA, IgD, or IgM, and the like), peptides, lipids (e.g., cholesterol, ceramides, and fatty acids), nucleic acids (e.g., RNA and DNA), small molecules (e.g., glucose, urea, and creatine), small molecule drugs or metabolites of small molecule drugs, microbes, inorganic molecules, elements, and ions (e.g., iron, $Ca^{2+}$, $K^+$, $Na^+$, and the like). In some embodiments, the biomolecule is exclusive of glucose and cancer markers.

In some embodiments, "drugs" may include abused drugs, such as, for example, cocaine, heroin, methyl amphetamine, and prescription drugs taken in excess of dosage, or taken without a prescription (e.g., painkillers such as opioids); and therapeutic drugs, such as, for example, tramadol, fluconazole, barbitals, and anabolic steroids.

In some embodiments, "warfare agents" may include any molecule, compound, or composition of either biological or chemical origin that may be used as a weapon. Non-limiting examples of warfare agents include explosives, nerve gases (e.g., VX and Sarin), phosgene, toxins, spores (e.g., anthrax), and the like.

In some embodiments, "environmental contaminants" may include any molecule, compound, or composition that can be detrimental to an individual, e.g., when at concentrations elevated above a risk threshold. Examples include water pollutants (e.g., fertilizers, pesticides, fungicides, insecticides, herbicides, heavy metals, and halides), soil pollutants (e.g., fertilizers, pesticides, fungicides, insecticides, herbicides, heavy metals, and halides), and air pollutants (e.g., $NO_x$, $SO_x$, greenhouse gases, persistent organic pollutants, particulate matter, and smog).

In some embodiments, solubilizing the target cells and tissue includes the application of energy. In some embodiments, the energy may be applied by any number of suitable methods, including mechanical (e.g., abrasion, shear, vacuum, pressure, suction, ultrasound), optical (e.g., laser), thermal, and electrical energy. However, in one embodiment, the energy does not include externally supplied thermal energy (i.e., heat). Suitable energy applicators are disclosed in U.S. patent application Ser. Nos. 12/664,994, 13/126,105, and 13/095,771, each of which is incorporated by reference herein in its entirety.

The compositions may be used for solubilizing cells for in vitro protein recovery. In addition to effective dissolution of cells, the compositions may provide a benefit of preservation of bioactivity. The compositions may also possess the ability to quickly solubilize various tissues, including those with durable mechanical properties, such as skin. To aid in the preservation of bioactivity, a protease inhibitor may be included in the compositions. However, with or without the addition of protease inhibitors, the compositions may be able to preserve the biological activity of proteins. The compositions are also applicable in vivo. In particular, the compositions may be able to recover labile phosphoproteins with RPPA, thus opening the possibility of quickly and non-invasively probing multiple signaling pathways.

In one embodiment, the compositions may be useful as antibacterial compositions. Thus, a method for inhibiting the growth and reproduction of bacteria and/or treating a bacterial infection is provided, the method comprising applying an antibacterial composition to an area that is subject to attack by the bacteria, the antibacterial composition comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58. The method may further include the application of energy.

In another embodiment, a method is provided for solubilizing cells and/or tissues, the method comprising contacting the cells and/or tissues with a composition, the composition comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58. In one embodiment, proteins, including cytosolic proteins, nuclear proteins, and surface proteins may be recovered from the solubilized cells and/or tissues. In some embodiments, such as, for example, embodiments where it is desirable to preserve biological activity of the proteins, the composition may further optionally comprise a protease inhibitor.

In one embodiment, the compositions may be used to probe protein functional states and related skin cell signaling pathways. Skin cell signaling pathways may be stress-induced, and may change over minutes to hours. Phosphorylation is a highly labile post-translational modification that regulates many aspects of protein function. The ability to probe these functional states in the epidermis necessitates a fast and efficient method to solubilize and isolate phosphoproteins. Thus, in another embodiment, a method is provided for recovering signaling proteins from skin cells, the method comprising: contacting the skin cells with a composition comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, to provide solubilized signaling proteins; and subjecting the solubilized signaling proteins to reverse phase protein array.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful for, among other things, disaggregating, solubilizing, and stabilizing cell components to be used as disease biomarkers, forensic biomarkers, or both. In one embodiment, the compositions are useful to disaggregate, solubilize, and stabilize components from living tissues in situ, from freshly resected tissues, frozen resected tissues, preserved paraffin embedded tissues, tissue and cell extracts and cultured cells derived from cell lines or resected tissues, and from exogenous agents such as viruses, bacteria, and prions.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful to solubilize, remodel, and remove diseased tissue on or beneath the surface of the skin, or elsewhere within the body. For example, the compositions may be useful to solubilize, remodel, and remove tissue hosting precancerous conditions such as actinic keratosis, leukoplakia, Barretts esophagus, and right-colon pre-cancer plaque, and surface cancers arising from any of these precancerous conditions. Other therapeutic uses may include solubilizing and removing tumors from a variety of surface or deep sites, or treating tumor surgical margins to remove any residual tumor cells at these sites. In some instances, after treating tumors with the compositions and solubilizing the constituent tumor markers, the immune system may detect the dissolved tumor markers and initiate a potent anti-tumor immune response against these markers, leading to regression of the local tumor, as well as destruction of any systemic tumor cells carrying the detected tumor markers.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful for treating skin lesions and damaged skin with therapeutic molecules and drugs that are unable to penetrate an intact outer skin barrier. More particularly, the compositions described herein may be useful to enhance absorption of topical therapeutics by removing diseased tissue, inflammatory cells, and thickened, hyper-keratinized skin that may block access to otherwise effective topical therapies. An example of such a use is as a pre-treatment for psoriasis topical therapies, since psoriasis lesions typically have a hardened top layer or hyperkeratosis that inhibits absorption. In one embodiment, such treatment may include perturbation of the outer skin barrier using the compositions, and in some circumstances applied energy, to disrupt the barrier by disaggregation and solubilization of barrier cells and tissues, followed by application of the therapeutic molecules and drugs directly to the surface of the barrier-perturbed skin. Example therapeutic molecules and drugs may include, for example, DNA-based drugs, RNA-based drugs, protein-based drugs, peptide-based drugs, lipid-based drugs, carbohydrate-based drugs, small molecule drugs, nanoparticle based drugs, liposome-encapsulated drugs, and combinations of such classes of drugs.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful for introducing therapeutic or diagnostic molecules and drugs into the body and bloodstream by disrupting the outer skin layer. In one embodiment, the introducing may include perturbation of the outer skin barrier using the compositions, and in some circumstances applied energy, to disrupt the barrier by disaggregation and solubilization of barrier cells and tissues, followed by application of the therapeutic or diagnostic molecules directly to the surface of the barrier-perturbed skin.

In another embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful to remove malignant and benign growths and obstructions in other organs in the body or within the central and peripheral nervous systems, including the eye, middle ear, brain, spinal cord, nerve roots, and ganglia. Since the compositions may dissociate and dissolve diseased tissue directly after injection through a thin needle or catheter, the compositions may allow ablative surgery in areas that are not accessible to either open surgery or even to minimally invasive surgical instruments (such as in the vascular system, including arteries and coronary arteries).

In another embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful to diminish or reduce intra-abdominal and peritoneal adhesions by dissolving specific bands of adherent tissue between intra-abdominal tissues and organs.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful for wound debridement. In one embodiment, the treatment may include contacting the compositions, and in some circumstances applied energy, to a wound's surrounding tissue to remove unhealthy tissue, including, for example, necrotic eschar and fibrinous slough.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful as a bio-glue to enhance post-operation healing.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful to promote oral and dental hygiene. For example, in one embodiment, the compositions may be useful to soften and/or dissolve hard and soft deposits on teeth and dentures.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful to solubilize, remodel, and remove cosmetically relevant structures on or beneath the surface of the skin. For example, in one embodiment, the compositions may be useful for treating aged, scarred, and UV-damaged skin, and removing and/or remodeling age spots, skin tags, seborrheic keratosis, scar tissues, xanthomas, non-cancerous hyperproliferative conditions, surface bumps, and scaly patches. In one embodiment, the use may include perturbation of the outer skin barrier using the compositions, and in some circumstances applied energy, to disrupt the barrier by disaggregation and solubilization of barrier cells and tissues. In one embodiment, the compositions may be introduced to deeper layers of skin to facilitate disaggregation, solubilization, and removal of structures associated with wrinkling, scarring, or both, of the skin surface. Other cosmetic uses include dermal peel or skin bleaching. The compositions may be used to remove discoloration of the skin associated with previous injury, UV-damage, or aging. In some embodiments, the perturbation may be followed by application of therapeutic drugs or natural products and other cosmetic compositions that are believed or known to increase the smoothness, elasticity, and resilience of skin. Such cosmetic compositions may include, for example, elastin or its peptides (e.g., V-V-P-Q), collagen or its peptides, resveratrol, idebenone, co-enzyme Q10, acetyl hexapeptide-3, glycosaminoglycans, palmitoyl pentapeptide-4, sodium hyaluronate, and the like, and combinations thereof.

In one embodiment, cell components recovered using the compositions may be introduced into biochemical assays to detect, quantify, and identify specific biomarkers associated with specific diseases. The biochemical assays may include all molecular diagnostic assays for detecting DNA, RNA, proteins, peptides, lipids, carbohydrates, and small molecules, both endogenous and exogenous. The biochemical assays to be used include PCR, ELISA, chromatography, gel analysis, electrophoresis, Western Blots, Southern Blots, Northern Blots, and other methods used in clinical laboratories for identification of molecular biomarkers of disease.

In one embodiment, the compositions comprising at least one of: (1) DPS and at least one of Brij 30, Brij 35, Brij 52, Brij C10, and Brij 58; (2) DDPS and at least one of Brij 30, Brij 35, Brij 52, Brij C10, and Brij 58; (3) TPS and at least one of Brij 30, Brij 35, Brij 52, Brij C10, and Brij 58; (4) HPS and at least one of Brij 30, Brij 35, Brij 52, Brij C10, and Brij 58; and (5) OPS and at least one of Brij 30, Brij 35, Brij 52, Brij C10, and Brij 58, may be useful in the treatment of mucosal and skin lesions. Such use may involve impregnating an abrasive and absorbent swab (similar to a for-daily-use facial exfoliating sponge) with one or more of the compositions, and applying the swab to the region of interest with medium pressure in a twisting or back-and-forth motion onto target tissue for a predetermined time. The depth may be controlled by the amount of pressure, as well as application time. After the lesion is dissolved and the released biomarkers are absorbed into the pad, the swab and the dissolved tissue may be collected and sent to, e.g., a pathology lab, for biomarker and other analyte analysis.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1

Materials

DPS, DDPS, TPS, HPS, and OPS were procured from Sigma-Aldrich as zwitterionic surfactants. Brij 35, Brij 52, Brij C10, and Brij 58 were procured from Sigma-Aldrich as nonionic surfactants. Brij 30 was procured from TCI America. All solutions were prepared by adding 0.25% w/v zwitterionic surfactant and 0.25% w/v nonionic surfactant (0.25% v/v B30), for a total concentration of 0.5% w/v in PBS (pH=7.4). A positive control was prepared by placing 1% v/v Triton X-100 (TX-1) in PBS.

Example 2

Protein Recovery from Porcine Skin

Protein was recovered from porcine skin as a model tissue. Skin was procured in frozen form from Lampire Biological Laboratories Inc., and stored at $-70°$ C. Two hours before use, skin was thawed at room temperature (RT) and cut into small pieces (2.5 cm×2.5 cm). Skin pieces were stripped off from subcutaneous fat and used without visible scratches or abrasions. Protein recovery was carried out by mounting the skin piece on a Franz diffusion cell (FDC) assembly (tissue exposure area of 1.77 cm$^2$; Permegear). The receiver chamber of the FDC was filled with PBS and the donor chamber was filled with 1 mL of surfactant combination as a sampling buffer. This buffer also acted as the coupling fluid between the ultrasound transducer and the tissue. Protein recovery was performed at RT with a 600-W probe sonicator (Sonics & Materials) operating at a frequency of 20 kHz. The ultrasound transducer was placed at a distance of 5 mm from the tissue surface and an ultrasonic intensity of 2.4 W/cm$^2$ at 50% duty cycle was applied for 3 min. The sampling buffer, now containing solubilized tissue constituents, was aspirated and kept at −70° C. until analysis.

The solubilization ability for each surfactant formulation disclosed herein was quantified by the concentrations of total protein and solubilized protein (mg/ml). Supernatants were isolated from the samples using a centrifuge operating at 10,000×g and 4° C. for 15 min. The solubilized protein amount was measured in the sample supernatant by using a colorimetric detection kit (Micro BCA Protein Assay Kit; Pierce).

Table 1 illustrates the total protein (mg/ml) recovered from porcine skin when the porcine skin is contacted with various combinations of zwitterionic and nonionic surfactants in the presence of ultrasound. FIG. 1 illustrates the same results in graphical form.

TABLE 1

|  | Brij 30 | Brij 35 | Brij 52 | Brij C10 | Brij 58 |
|---|---|---|---|---|---|
| DPS | 1.47 ± 0.26 | 1.67 ± 0.20 | 1.33 ± 0.46 | 1.44 ± 0.23 | 1.69 ± 0.33 |
| DDPS | 1.68 ± 0.25 | 1.90 ± 0.43 | 1.95 ± 0.44 | 2.11 ± 0.29 | 1.84 ± 0.23 |
| TPS | 1.95 ± 0.26 | 1.79 ± 0.05 | 2.23 ± 0.25 | 2.33 ± 0.36 | 1.52 ± 0.19 |
| HPS | 2.19 ± 0.05 | 1.68 ± 0.26 | 2.32 ± 0.29 | 1.98 ± 0.31 | 1.64 ± 0.39 |
| OPS | 2.15 ± 0.54 | 1.71 ± 0.19 | 2.22 ± 0.23 | 2.42 ± 0.36 | 1.88 ± 0.32 |

Figure 2:
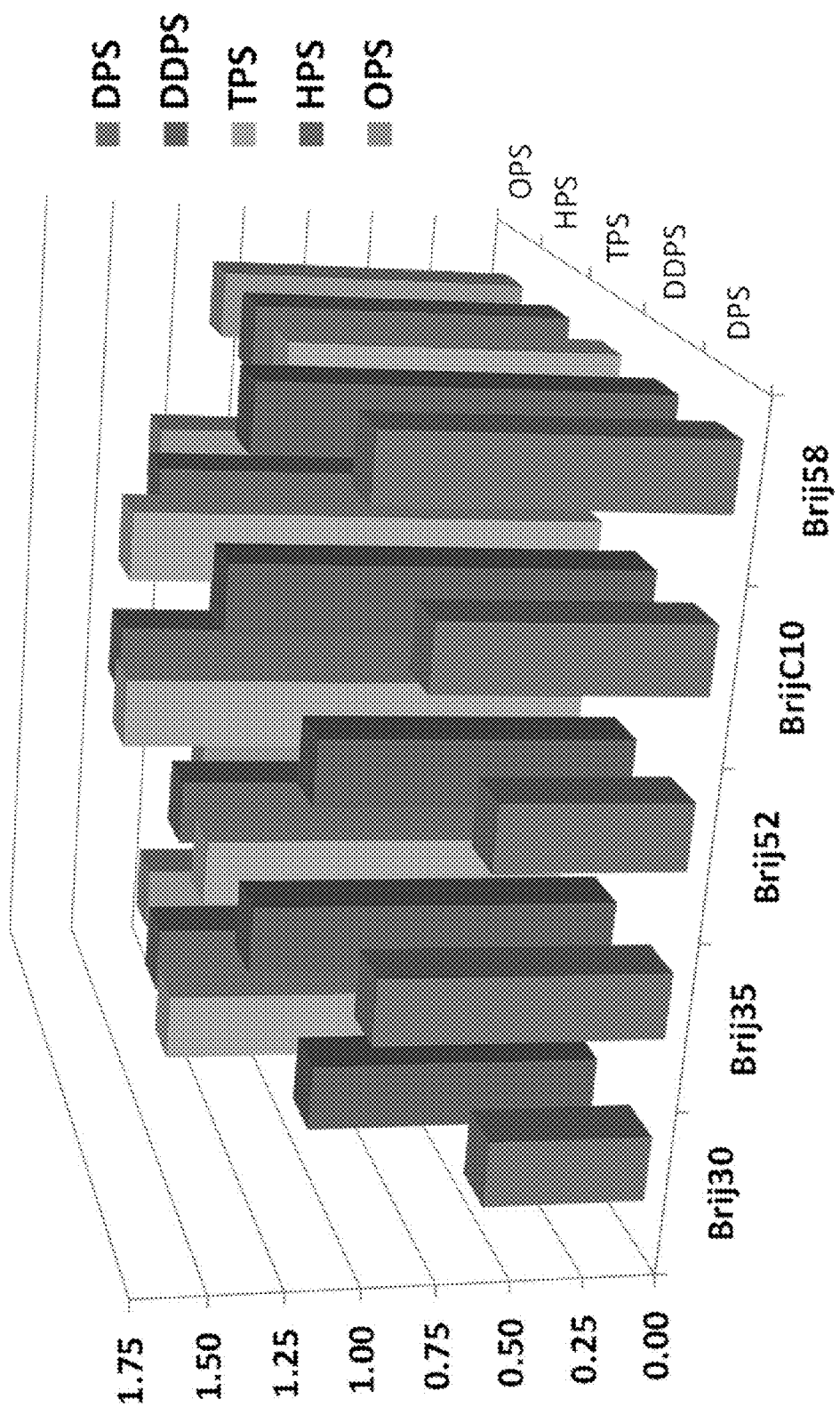
FIG. 2 illustrates in graphical form the soluble protein (mg/ml) recovered from porcine skin when the porcine skin is contacted with various combinations of zwitterionic and non-ionic surfactants in the presence of ultrasound.

Table 2 illustrates the soluble protein (mg/ml) recovered from porcine skin when the porcine skin is contacted with those same combinations of zwitterionic and nonionic surfactants in the presence of ultrasound. FIG. 2 illustrates the results in graphical form.

TABLE 2

|  | Brij 30 | Brij 35 | Brij 52 | Brij C10 | Brij 58 |
|---|---|---|---|---|---|
| DPS | 0.56 ± 0.04 | 0.99 ± 0.30 | 0.65 ± 0.03 | 0.91 ± 0.13 | 1.15 ± 0.07 |
| DDPS | 1.02 ± 0.12 | 1.27 ± 0.19 | 1.10 ± 0.12 | 1.44 ± 0.16 | 1.39 ± 0.22 |
| TPS | 1.40 ± 0.26 | 1.31 ± 0.15 | 1.63 ± 0.16 | 1.64 ± 0.33 | 1.16 ± 0.25 |
| HPS | 1.34 ± 0.27 | 1.29 ± 0.26 | 1.55 ± 0.13 | 1.45 ± 0.18 | 1.15 ± 0.29 |
| OPS | 1.27 ± 0.28 | 1.09 ± 0.14 | 1.06 ± 0.25 | 1.34 ± 0.20 | 1.14 ± 0.16 |

Example 3

Concentration Dependence

Figure 3:
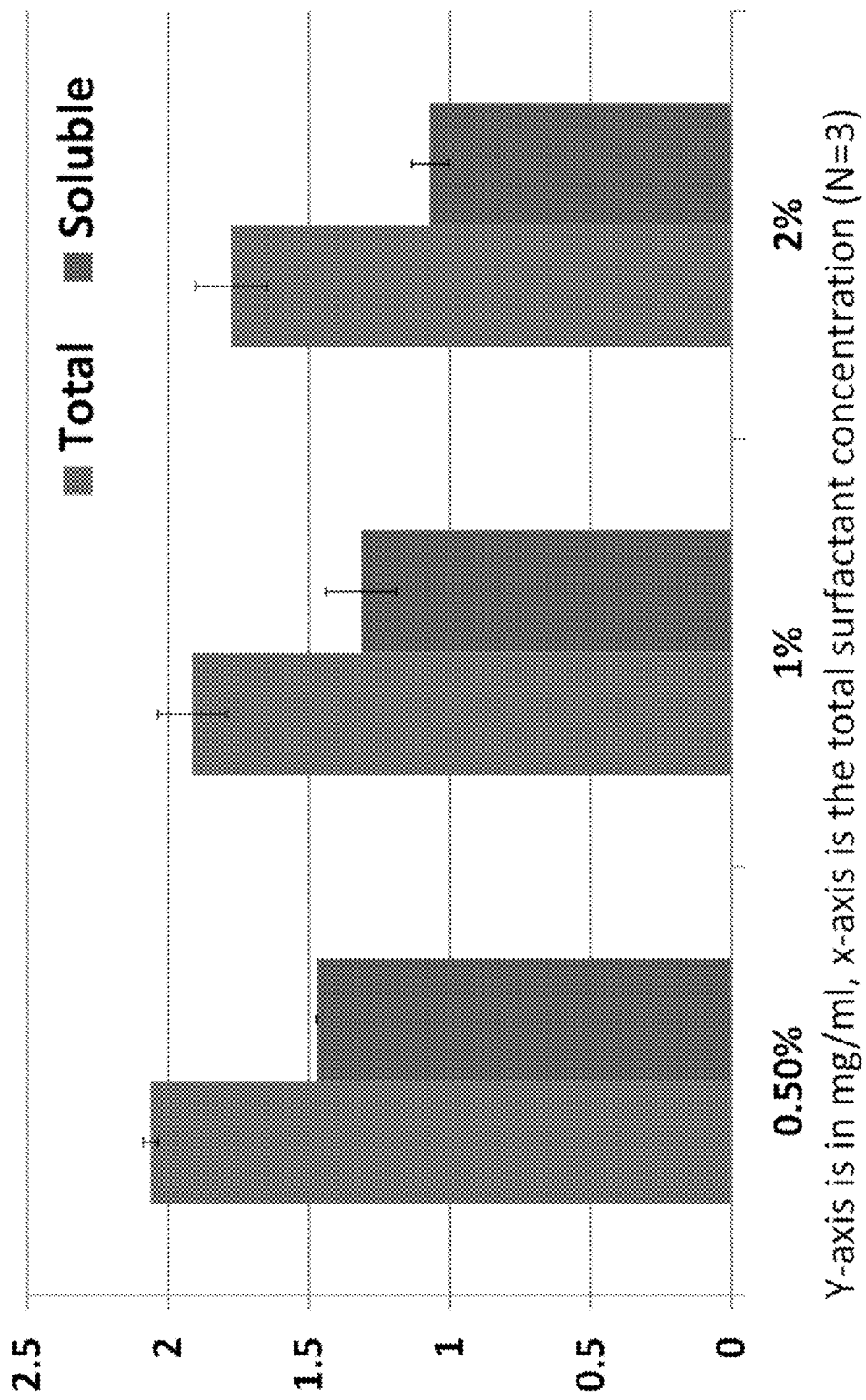
FIG. 3 illustrates the dependence on concentration of the protein extraction efficacy from porcine skin of TPS:Brij C10.

TPS:Brij C10 was investigated for concentration effect. The surfactant concentration was tested at total concentrations of 0.5%, 1%, and 2% of TPS:Brij C10, at a 1:1 ratio. FIG. 3 illustrates the dependence on concentration of TPS: Brij C10 on the soluble and total protein extraction efficacy from porcine skin.

Example 4

Enzyme Protection

Figure 4:
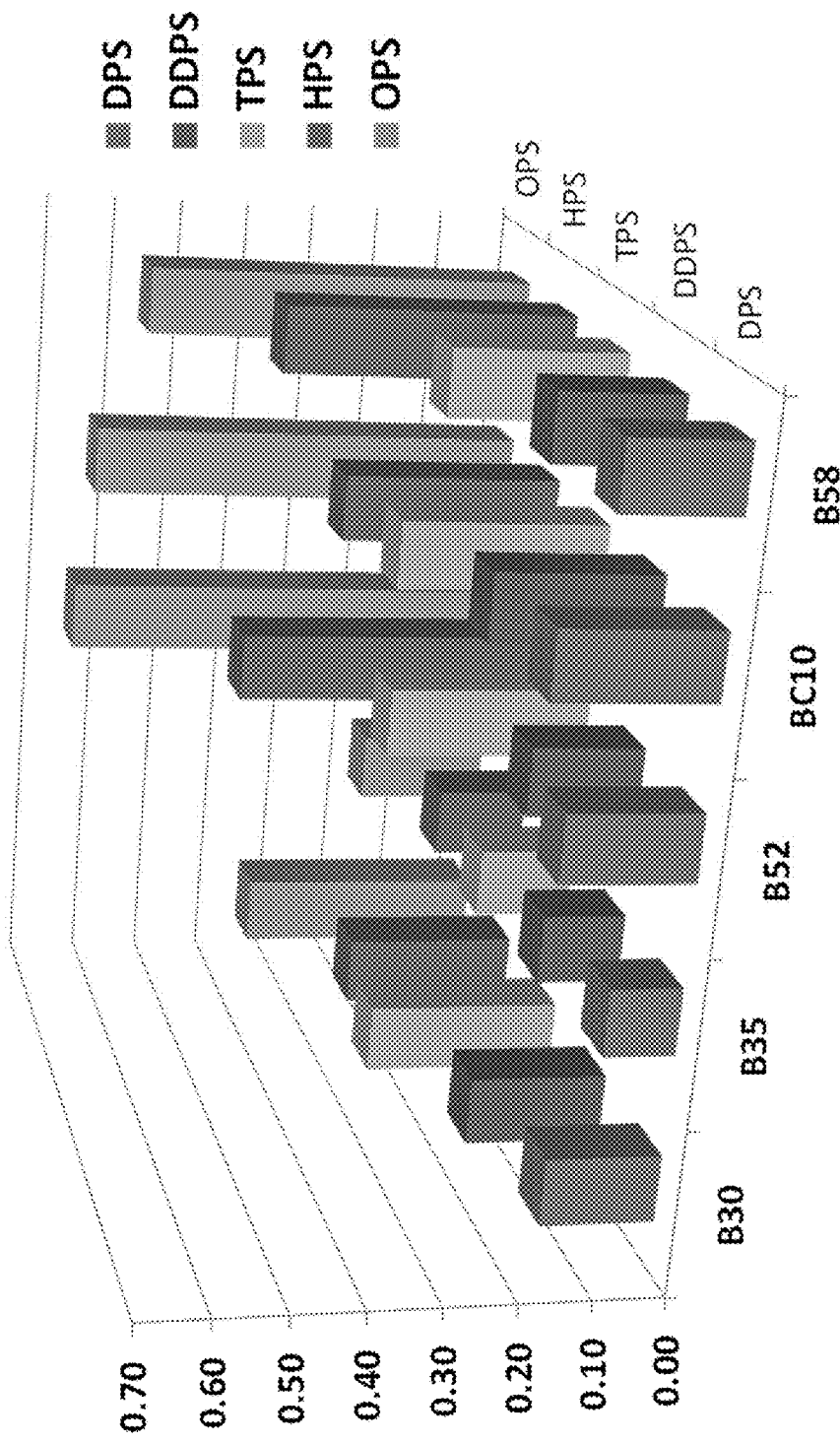
FIG. 4 illustrates in graphical form the preserved activity of the intracellular enzyme glyceraldehyde 3-phosphate dehydrogenase (GAPDH) in various combinations of zwitterionic and nonionic surfactants.

GAPDH from rabbit was procured as a model enzyme from Sigma-Aldrich. GAPDH powder was dissolved in ddH$_2$O (Milipore) to 90 U/ml and distributed into an E-tube, then stored at −80° C. until use. Enzyme protection was carried out by incubation of GAPDH in each combination disclosed herein, compared to that in PBS as a positive control. The concentration of GAPDH was fixed to 0.5 U/ml. GAPDH was incubated at 37° C. for 10 min. The activity of the GAPDH enzyme (U/ml) was assessed by KDalert™ GAPDH Assay Kit (Ambion, Inc, TX, USA). FIG. 4 illustrates in graphical form the preserved activity of GAPDH in each of the various combinations of zwitterionic and nonionic surfactants.

Figure 5:
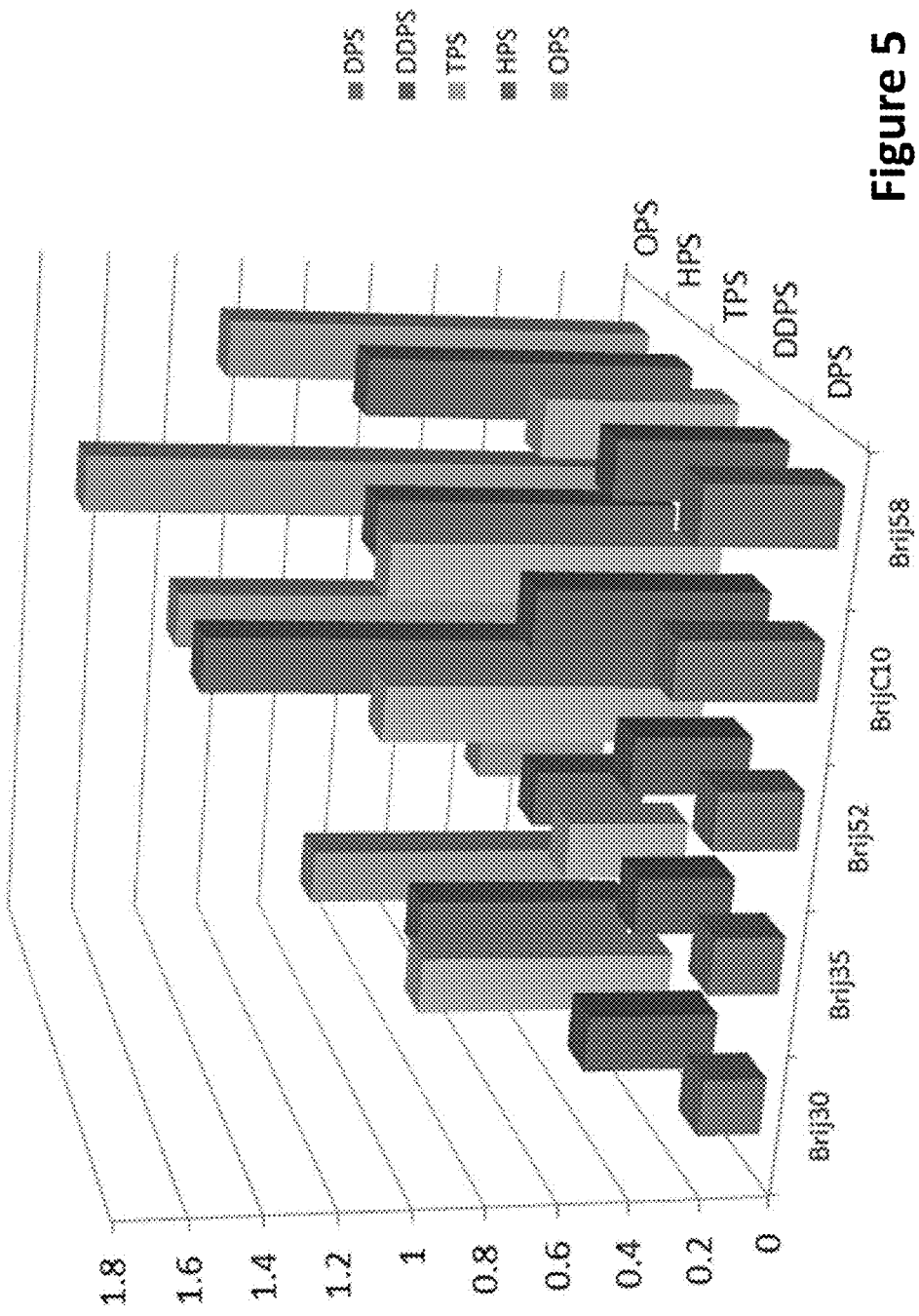
FIG. 5 illustrates in graphical form the combined dependence of soluble protein extraction efficacy and GAPDH stability in various combinations of zwitterionic and nonionic surfactants.

GAPDH activities were multiplied by soluble protein recovery. FIG. 5 illustrates in graphical form the combined dependence of soluble protein extraction efficacy and GAPDH stability in each of the various combinations of zwitterionic and nonionic surfactants.

Example 5

Cell Solubilization

Figure 6:
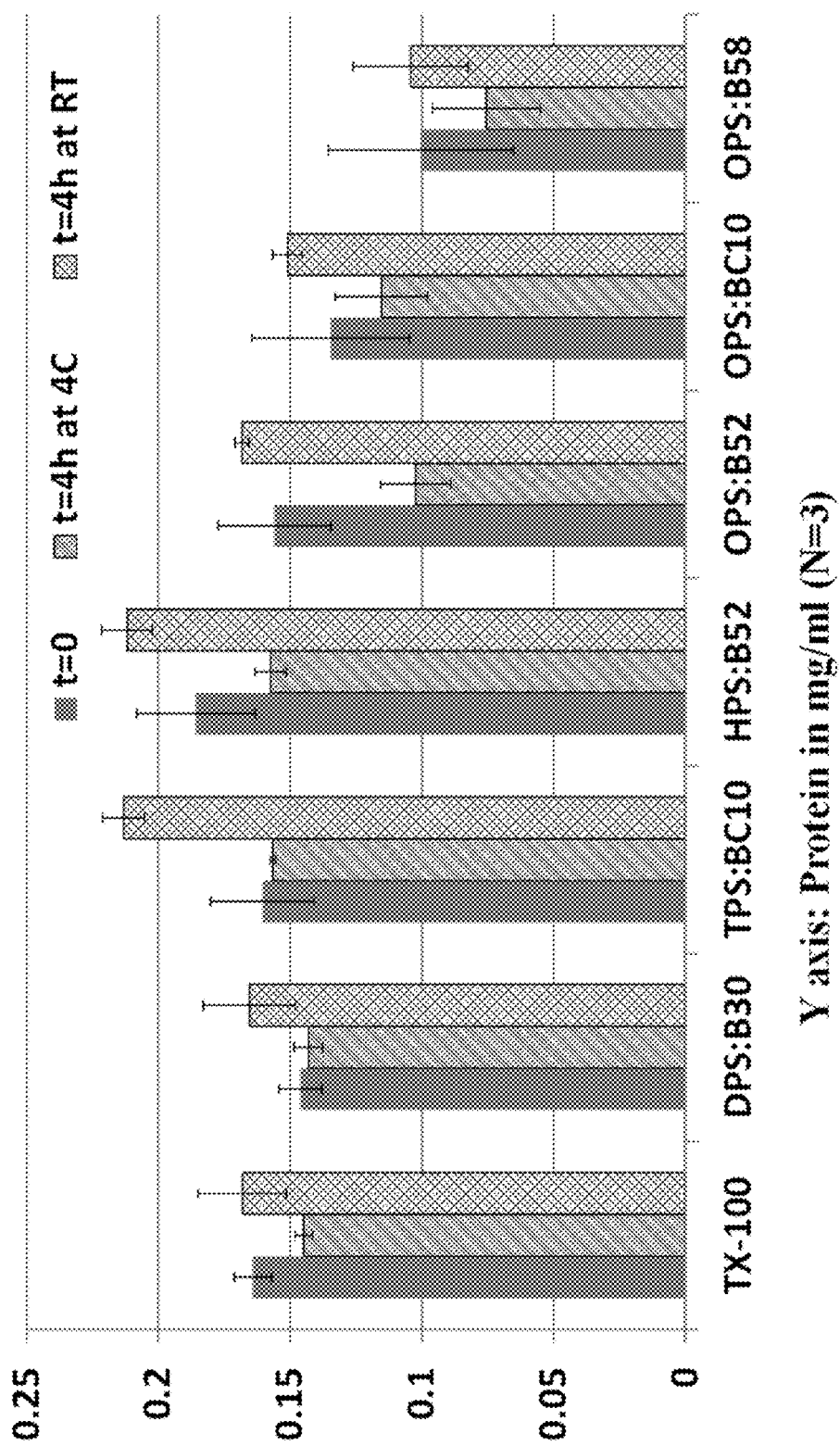
FIG. 6 illustrates the total protein recovery from Human Epidermal Keratinocyte (HEK) cells at t=0 (solid bars), t=4 hours at 4° C. (diagonal bars), and t=4 hours at RT (cross-hatched bars), using various reagents.

HEK cells (HEKa-APF, Invitrogen, CA, USA) were cultured in a Corning® cell culture treated flask with a Vent Cap (75 cm$^2$ Rectangular Canted Neck, Corning). The HEK cells were grown between passage 3 to 8 in the EpiLife® Medium with 60 μM calcium added by Human Keratinocyte Growth Supplement. FIG. 6 illustrates the total protein recovery from HEK cells at t=0 (solid bars), t=4 hours at 4° C. (diagonal bars), and t=4 hours at RT (cross-hatched bars), using DPS: Brij 30, TPS:Brij C10, HPS:Brij 52, OPS:Brij 52, OPS:Brij C10, and OPS:Brij 58, as compared to TX-1.

Example 6

In Vitro Assay

Total protein in solubilized cells was analyzed using a Micro BCA

Figure 7:
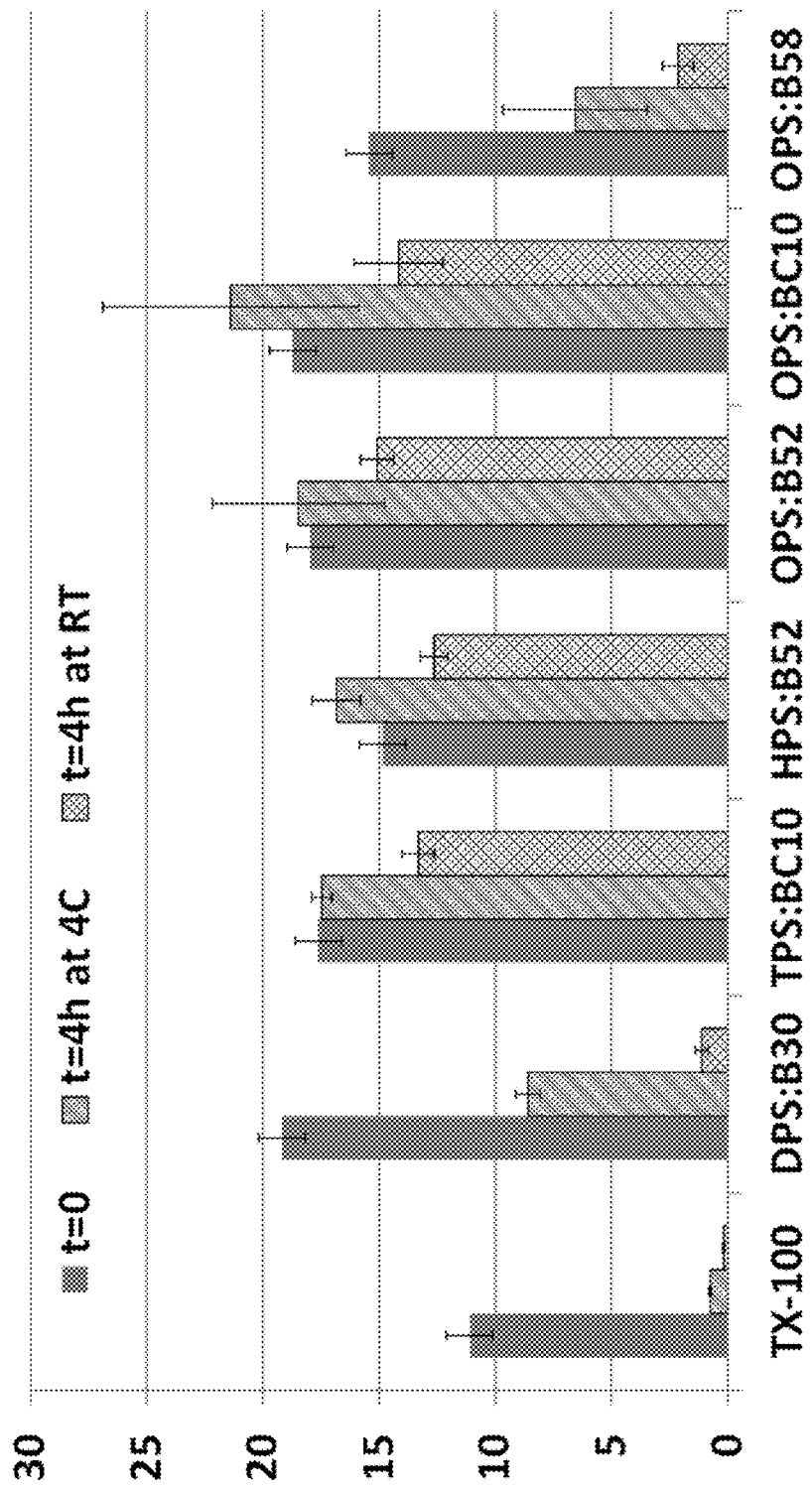
FIG. 7 illustrates the GAPDH activity measured in HEK cells solubilized in various reagents, at t=0 (solid bars), t=4 hours at 4° C. (diagonal bars), and t=4 hours at RT (cross-hatched bars).

Protein Assay Kit (Fisher Scientific, PA, USA). Trypsinized cells were counted by hemocytometer (Fisher Scientific, PA, USA) and added to 96-well plates. After overnight growth, the medium was removed and replaced by 100 μl of lysis agents (TX-1, DPS:Brij 30, TPS:Brij C10, HPS: Brij 52, OPS:Brij 52, OPS:Brij C10, and OPS:Brij 58). FIG. 7 illustrates the GAPDH activity measured in HEK cells solubilized in those same reagents, at t=0 (solid bars), t=4 hours at 4° C. (diagonal bars), and t=4 hours at RT (cross-hatched bars).

Figure 8:
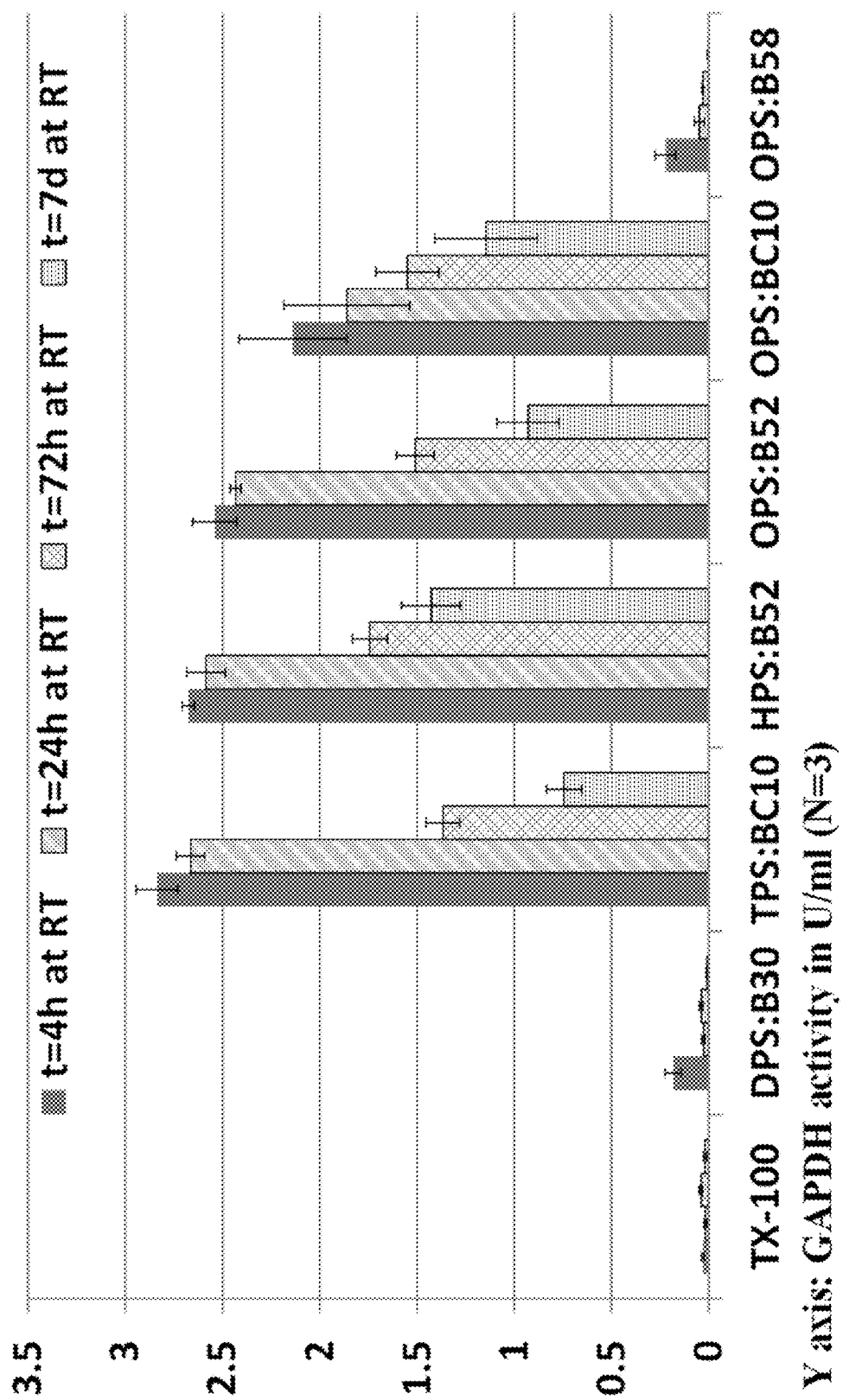
FIG. 8 illustrates the GAPDH activity measured in HEK cells solubilized in various reagents, at room temperature at t=4 hours (solid bars), t=24 hours (diagonal bars), 72 hours (cross-hatched bars), and 7 days (horizontal bars).

For further study of stability, the enzymes were incubated for one day at RT, three days at RT, and seven days at RT. FIG. 8 illustrates the GAPDH activity measured at RT, at t=4 hours (solid bars), t=24 hours (diagonal bars), t=72 hours (cross-hatched bars), and 7 days (horizontal bars).

Example 7

Tissue Solubilization

Figure 9:
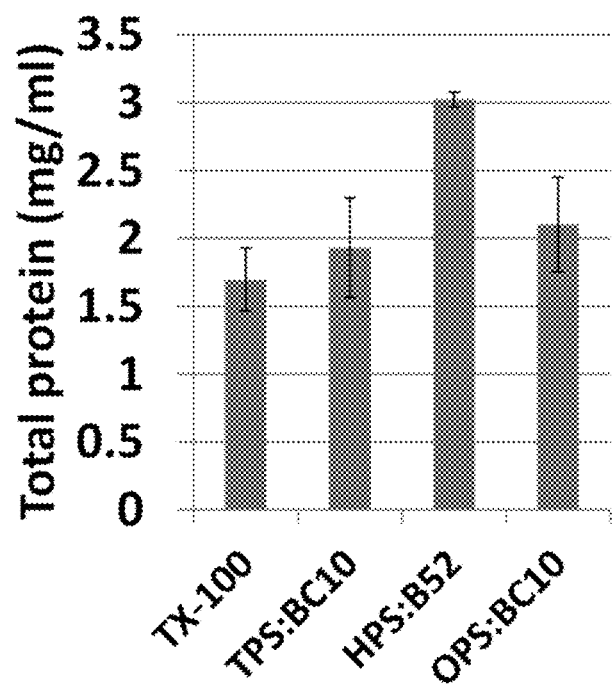
FIG. 9 illustrates the total protein recovered from homogenized mouse skin using various reagents.
Figure 10:
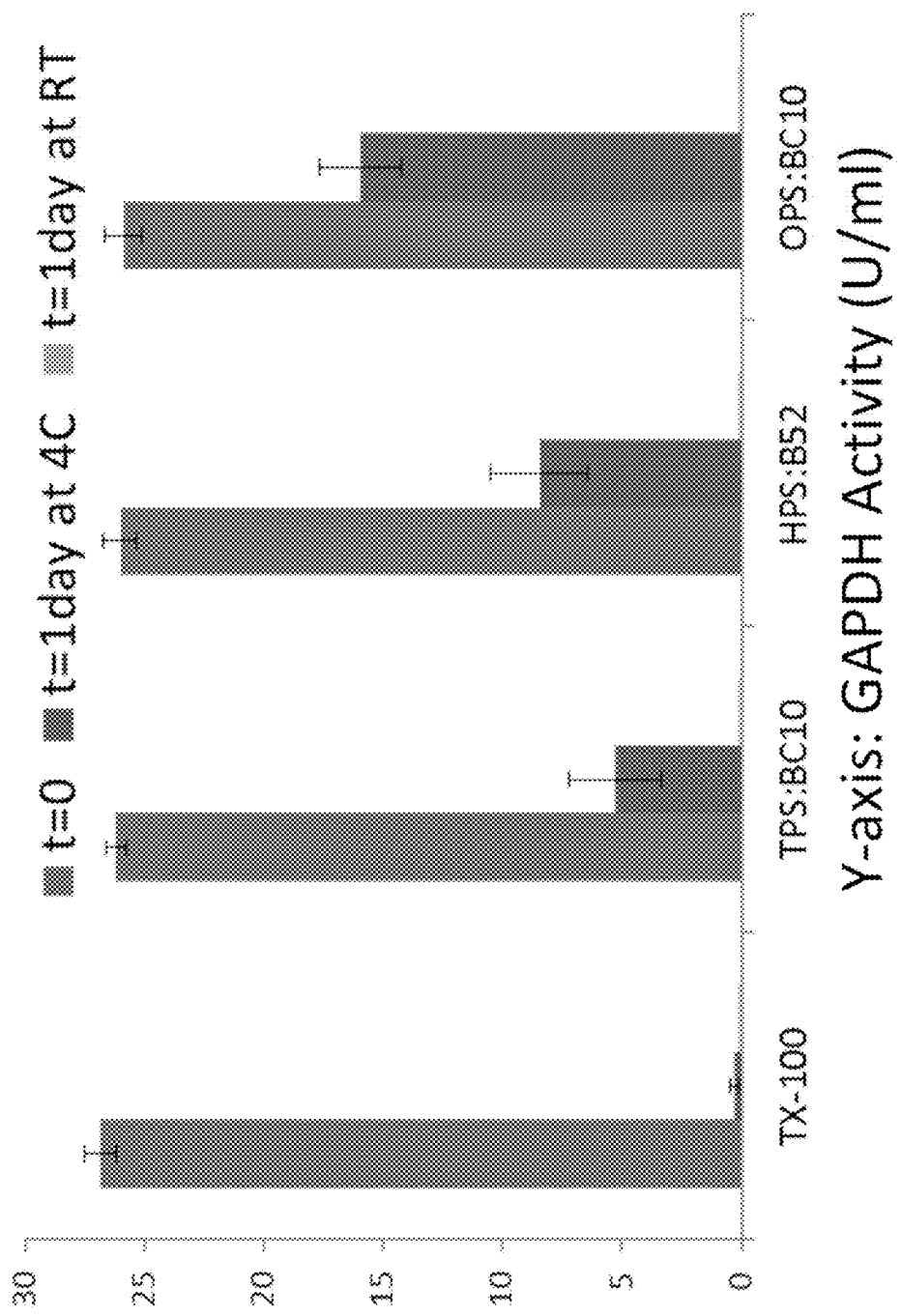
FIG. 10 illustrates the specific GAPDH activity measured in homogenized mouse skin using various reagents.

Skin tissue was collected from euthanized mice and stored at −80° C. until use. About 10 mg of each tissue was placed in a 2 ml tube. 400 μl of chilled lysis buffer (TX-1, TPS:Brij C10, HPS:Brij 52, and OPS:Brij C10) and protease inhibitor cocktail tablets (Roche Applied Science, IN, USA) were added to the tube (one tablet per 50 ml; one tablet contains Antipain-dihydrochloride 3 mg, Aprotinin 0.5 mg, Bestatin 0.5 mg, Chymostatin 1 mg, E-64 3 mg, EDTA-Na$_2$ 10 mg, Leupeptin 0.5 mg, Pefabloc SC 20 mg, Pepstatin 0.5 mg, and Phosphoramidon 3 mg). Tissue was homogenized using a homogenizer (IKA, NC, USA) at 13,000 rpm for 1 min. FIG. 9 illustrates the total protein recovered from homogenized mouse skin using TPS:Brij C10, HPS:Brij 52, and OPS:Brij C10, as compared to TX-1. FIG. 10 illustrates the specific GAPDH activity measured in the homogenized mouse skin.

To the extent that the term "includes" or "including" is used in the specification or the claims, it is intended to be inclusive in a manner similar to the term "comprising" as that term is interpreted when employed as a transitional word in a claim. As used in the specification and the claims, the singular forms "a," "an," and "the" include the plural. Furthermore, to the extent that the term "or" is employed (e.g., A or B), it is intended to mean "A or B or both." Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, with the benefit of the disclosure provided in this application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A composition, comprising:
   N-tetradecyl-N,N-dimethyl-3-ammonio-1-propane-sulfonate; and
   polyoxyethylene (10) cetyl ether.

2. The composition of claim 1, wherein the composition has a pH more basic than about 7.0 in a buffer solution.

3. The composition of claim 1, wherein the composition has a pH of between about 7.0 and about 9.0 in a buffer solution.

4. The composition of claim 1, further comprising a buffer solution that dissolves the N-tetradecyl-N,N-dimethyl-3-ammonio-1-propanesulfonate and the polyoxyethylene (10) cetyl ether, one or both of the N-tetradecyl-N,N-dimethyl-3-ammonio-1-propanesulfonate and the polyoxyethylene (10) cetyl ether each being in an amount of about 0.25% w/v with respect to the buffer solution.

5. A method for solubilizing and remodeling and/or removing tissue on or beneath a patient's skin, the method comprising:
   applying energy to a region of interest on the skin; and
   contacting the region with a tissue solubilizing composition, the tissue solubilizing composition comprising:
   N-tetradecyl-N,N-dimethyl-3-ammonio-1-propane-sulfonate; and
   polyoxyethylene (10) cetyl ether.

6. The method of claim 5, further comprising:
   removing at least a portion of the solubilized region of interest to leave an exposed area on the skin; and
   applying to the exposed area at least one of a therapeutic composition and a cosmetic composition.

7. The method of claim 6, wherein the applying comprises applying to the exposed area a therapeutic composition comprising at least one of a DNA-based drug, an RNA-based drug, a protein-based drug, a peptide-based drug, a lipid-based drug, a carbohydrate-based drug, a small molecule drug, a nanoparticle-based drug, and a liposome-encapsulated drug.

8. The method of claim 6, wherein the applying comprises applying to the exposed area a cosmetic composition comprising at least one of elastin, an elastin-based peptide, collagen, a collegen-based peptide, resveratrol, idebenone, coenzyme Q10, acetyl hexapeptide-3, glycosaminoglycans, palmitoyl pentapeptide-4, sodium hyaluronate, and combinations thereof.

9. A method for recovering analytes from mucosal membrane, skin, or other tissue, the method comprising:
   applying energy to a region of interest on the mucosal membrane, skin, or other tissue containing at least one analyte;
   contacting the region with a tissue solubilizing composition, thereby solubilizing at least some of the mucosal membrane, skin, or other tissue containing at least one analyte,
   wherein the tissue solubilizing composition comprises:
   N-tetradecyl-N,N-dimethyl-3-ammonio-1-propane-sulfonate; and
   polyoxyethylene (10) cetyl ether; and
   collecting the at least one analyte from the solubilized mucosal membrane, skin, and other tissue.

10. The method of claim 9, wherein the analyte comprises a protein.

11. The method of claim 9, wherein the analyte comprises a cancer biomarker.

12. The method of claim 9, wherein the analyte comprises an antibody.

13. The method of claim 9, wherein the analyte comprises a peptide.

14. The method of claim 9, wherein the analyte comprises a lipid.

15. The method of claim 9, wherein the analyte comprises a nucleic acid.

16. The method of claim 9, wherein the analyte comprises a small molecule.

17. The method of claim 9, wherein the analyte comprises a microbe.

18. The method of claim 9, wherein the analyte comprises a warfare agent.

19. The method of claim 9, wherein the analyte comprises an environmental contaminant.

20. The method of claim 9, wherein the analyte comprises a drug.

* * * * *